United States Patent
Piron et al.

(10) Patent No.: US 11,576,726 B2
(45) Date of Patent: Feb. 14, 2023

(54) SYSTEM AND METHOD FOR PROVIDING SURGICAL GUIDANCE BASED ON POLARIZATION-SENSITIVE OPTICAL COHERENCE TOMOGRAPHY

(71) Applicant: SYNAPTIVE MEDICAL INC., Toronto (CA)

(72) Inventors: Cameron Anthony Piron, Toronto (CA); Michael Frank Gunther Wood, Toronto (CA); Murugathas Yuwaraj, Toronto (CA); Siu Wai Jacky Mak, Toronto (CA)

(73) Assignee: Synaptive Medical Inc.

( * ) Notice: Subject to any disclaimer, the term of this patent is extended or adjusted under 35 U.S.C. 154(b) by 960 days.

(21) Appl. No.: 16/368,533

(22) Filed: Mar. 28, 2019

(65) Prior Publication Data

US 2019/0216545 A1 Jul. 18, 2019

Related U.S. Application Data

(62) Division of application No. 15/313,818, filed as application No. PCT/CA2016/050105 on Feb. 5, 2016, now Pat. No. 10,285,761.

(51) Int. Cl.
*A61B 34/10* (2016.01)
*A61B 5/00* (2006.01)
*A61B 34/00* (2016.01)
*A61B 90/00* (2016.01)
*G01B 9/02* (2022.01)
(Continued)

(52) U.S. Cl.
CPC ............ *A61B 34/10* (2016.02); *A61B 5/00* (2013.01); *A61B 5/0066* (2013.01); *A61B 34/00* (2016.02); *A61B 90/37* (2016.02); *G01B 9/02091* (2013.01); *A61B 5/0035* (2013.01); *A61B 5/0084* (2013.01); *A61B 17/3421* (2013.01); *A61B 2034/107* (2016.02);
(Continued)

(58) Field of Classification Search
CPC ............ A61B 17/342; A61B 2034/107; A61B 2034/2055; A61B 2090/365; A61B 2090/3735; A61B 34/10; A61B 5/0066; A61B 34/00; A61B 5/00; A61B 90/37
See application file for complete search history.

(56) References Cited

U.S. PATENT DOCUMENTS 8,237,835 B1 * 8/2012 Muller .................. G02B 21/14
382/128
9,526,412 B2 * 12/2016 Yang .................... A61B 3/1225
(Continued)

*Primary Examiner* — Baisakhi Roy

(57) ABSTRACT

Systems and methods are provided for identifying a suitable surgical location and/or trajectory for proceeding with a surgical procedure based on local polarization-sensitive optical coherence tomography imaging (PS-OCT). PS-OCT images are obtained of a tissue region and are processed to provide a spatial map of anisotropic structure within the tissue region. The anisotropic structure is processed to determine one or more suitable surgical locations and/or trajectories for avoiding or reducing damage to local anisotropic tissue structure identified within the tissue region. The spatial map of the anisotropic structure is registered with pre-operative volumetric image data identifying anisotropic tissue structure within a second tissue region that is larger than the tissue region imaged by PS-OCT.

7 Claims, 18 Drawing Sheets

(51) Int. Cl.
 *G01B 9/02091* (2022.01)
 *A61B 17/34* (2006.01)
 *A61B 34/20* (2016.01)
 *G01N 21/47* (2006.01)

(52) U.S. Cl.
 CPC . *A61B 2034/2055* (2016.02); *A61B 2090/365* (2016.02); *A61B 2090/3735* (2016.02); *G01N 21/4795* (2013.01)

(56) References Cited

U.S. PATENT DOCUMENTS

| | | | |
|---|---|---|---|
| 9,612,105 B2* | 4/2017 | Kemp | A61B 5/0084 |
| 9,760,688 B2* | 9/2017 | McIntyre | G16H 50/50 |
| 10,241,028 B2* | 3/2019 | Rowe | G01N 15/0205 |
| 2008/0180683 A1* | 7/2008 | Kemp | G01B 9/02028 |
| | | | 356/491 |
| 2013/0245461 A1* | 9/2013 | Maier-Hein | A61B 34/10 |
| | | | 600/476 |
| 2016/0015469 A1* | 1/2016 | Goshayesh | A61B 1/000094 |
| | | | 600/424 |
| 2018/0049642 A1* | 2/2018 | Mak | G01B 9/02091 |

\* cited by examiner

SYSTEM AND METHOD FOR PROVIDING SURGICAL GUIDANCE BASED ON POLARIZATION-SENSITIVE OPTICAL COHERENCE TOMOGRAPHY

BACKGROUND

The present disclosure is generally related to image guided medical procedures.

Port-based surgery allows a surgeon, or robotic surgical system, to perform a surgical procedure involving tumor resection in which the residual tumor remaining after is minimized, while also minimizing the trauma to the intact white and grey matter of the brain. In such procedures, trauma may occur, for example, due to contact with the access port, stress to the brain matter, unintentional impact with surgical devices, and/or accidental resection of healthy tissue.

Current technology to generate tractography information of the brain is through the use of magnetic resonance imaging (MRI). MRI images are typically taken hours before the surgery and require co-registration to a patient's stereotactic head frame. This is a costly approach and requires significant patient preparation. More importantly, these dated images deviate from the actual anatomy of the brain during the surgery due to the brain dynamics and affection of the surgery, which misguide the surgeon and impose potential risk to the surgery. These images are also static which provides no feedback to the surgeon during the surgery. Tractography information could potentially be obtained with intraoperative real-time MRI. This requires patient's head to rest inside an MR imaging head coil and fixed within the fixation frame throughout the surgery. The use of MRI introduces significant cost to the operating room (OR) setup. The sophisticated setup delays surgical procedures and extends the surgery.

SUMMARY

Systems and methods are provided for identifying a suitable surgical location and/or trajectory for proceeding with a surgical procedure based on local polarization-sensitive optical coherence tomography imaging. In one embodiment, polarization-sensitive optical coherence tomography images are obtained of a tissue region, and the polarization-sensitive optical coherence tomography images are processed to provide a spatial map of anisotropic structure within the tissue region. The anisotropic structure may be processed to determine one or more suitable surgical locations and/or trajectories for avoiding or reducing damage to local anisotropic tissue structure identified within the tissue region. The spatial map of the anisotropic structure may be registered with pre-operative volumetric image data identifying anisotropic tissue structure within a second tissue region that is larger than, and includes, the tissue region imaged by polarization-sensitive optical coherence tomography.

Accordingly, in one aspect, there is provided a method of identifying a suitable surgical location for proceeding with a surgical procedure based on local polarization-sensitive optical coherence tomography imaging, the method comprising:

obtaining one or more polarization-sensitive optical coherence tomography images of a tissue region;

processing the one or more polarization-sensitive optical coherence tomography images to generate local volumetric image data, the local volumetric image data providing a spatial map of anisotropic structure within the tissue region;

processing the local volumetric image data to determine one or more suitable surgical locations for avoiding or reducing damage to local anisotropic tissue structure identified within the tissue region when proceeding with a surgical procedure; and identifying at least one suitable surgical location on a display device.

In another aspect, there is provided a method of determining risk of proceeding with a surgical procedure based on local polarization-sensitive optical coherence tomography imaging, the method comprising:

obtaining one or more polarization-sensitive optical coherence tomography images of a tissue region;

processing the one or more polarization-sensitive optical coherence tomography images to generate local optical volumetric image data, the local optical volumetric image data providing a spatial map of anisotropic structure within the tissue region;

registering the local optical volumetric image data to a reference frame associated with a surgical plan, the surgical plan comprising one or more planned entry points for entering the tissue region; and processing the local optical volumetric image data to determine a risk measure associated with one or more of the planned entry points based on the presence of local anisotropic tissue structure identified within the tissue region.

In another aspect, there is provided a method of performing local optical imaging of anisotropic tissue structures, the method comprising:

obtaining one or more polarization-sensitive optical coherence tomography images of a tissue region;

processing the one or more polarization-sensitive optical coherence tomography images to generate local optical volumetric image data associated with the tissue region, the local optical volumetric image data providing a spatial map of anisotropic structure within the tissue region;

obtaining pre-operative volumetric image data, the pre-operative volumetric image data including the tissue region;

registering the local optical volumetric image data to the pre-operative volumetric image data;

generating a composite tractography image based on the local optical volumetric image data and the pre-operative volumetric image data; and presenting the composite tractography image on a display device.

In another aspect, there is provided a method of performing local optical imaging of anisotropic tissue structures, the method comprising:

obtaining, with a spatially tracked polarization-sensitive optical coherence tomography probe, one or more polarization-sensitive optical coherence tomography images of a tissue region;

processing the one or more polarization-sensitive optical coherence tomography images to generate local optical volumetric image data associated with the tissue region, the local optical volumetric image data providing a spatial map of anisotropic structure residing within the tissue region;

obtaining pre-operative volumetric image data within a patient reference frame, the pre-operative volumetric image data including the tissue region;

employing a tracked position and orientation of the spatially tracked polarization-sensitive optical coherence tomography probe to transform the local optical volumetric image data into the patient reference frame;

generating a composite tractography image based on the local optical volumetric image data and the pre-operative volumetric image data; and presenting the composite image on a display device.

A further understanding of the functional and advantageous aspects of the disclosure can be realized by reference to the following detailed description and drawings.

BRIEF DESCRIPTION OF THE DRAWINGS

Embodiments will now be described, by way of example only, with reference to the drawings, in which.

DETAILED DESCRIPTION

Figure 1A:
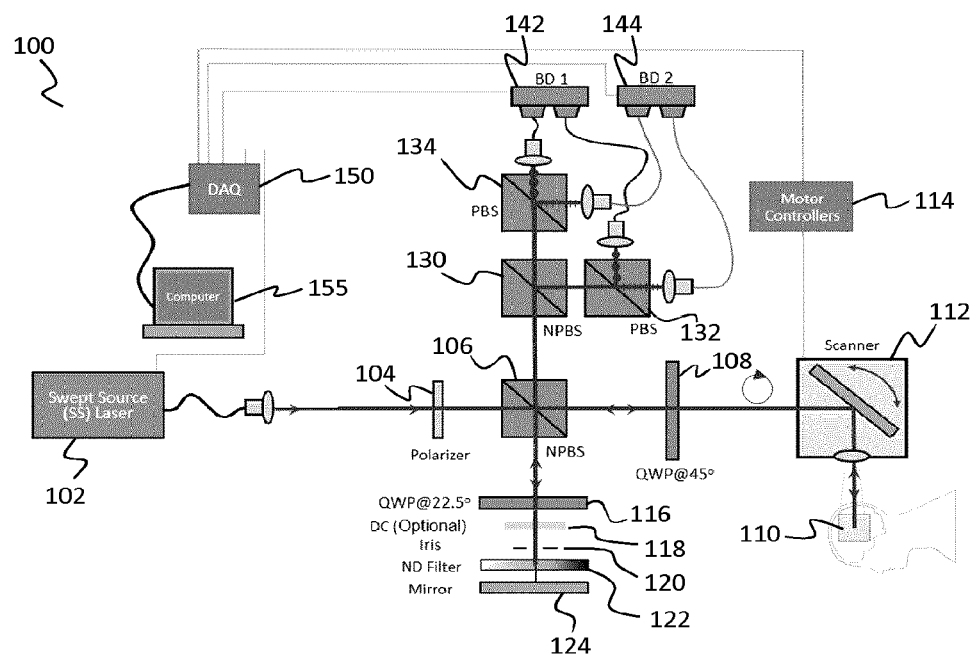
FIG. 1A illustrates an example embodiment of a free-space OCT System.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

As used herein, the terms, "comprises" and "comprising" are to be construed as being inclusive and open ended, and not exclusive. Specifically, when used in the specification and claims, the terms, "comprises" and "comprising" and variations thereof mean the specified features, steps or components are included. These terms are not to be interpreted to exclude the presence of other features, steps or components.

As used herein, the term "exemplary" means "serving as an example, instance, or illustration," and should not be construed as preferred or advantageous over other configurations disclosed herein.

As used herein, the terms "about" and "approximately" are meant to cover variations that may exist in the upper and lower limits of the ranges of values, such as variations in properties, parameters, and dimensions. In one non-limiting example, the terms "about" and "approximately" mean plus or minus 10 percent or less.

It is to be understood that unless otherwise specified, any specified range or group is as a shorthand way of referring to each and every member of a range or group individually, as well as each and every possible sub-range or sub-group encompassed therein and similarly with respect to any sub-ranges or sub-groups therein. Unless otherwise specified, the present disclosure relates to and explicitly incorporates each and every specific member and combination of sub-ranges or sub-groups.

As used herein, the term "on the order of", when used in conjunction with a quantity or parameter, refers to a range spanning approximately one tenth to ten times the stated quantity or parameter.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrases "access port" and "surgical access port" refer to a cannula, conduit, sheath, port, tube, or other structure that is insertable into a subject, in order to provide access to internal tissue, organs, or other biological substances. In some embodiments, an access port may directly expose internal tissue, for example, via an opening or aperture at a distal end thereof, and/or via an opening or aperture at an intermediate location along a length thereof. In other embodiments, an access port may provide indirect access, via one or more surfaces that are transparent, or partially transparent, to one or more forms of energy or radiation, such as, but not limited to, electromagnetic waves and acoustic waves.

As used herein the phrase "intraoperative" refers to an action, process, method, event or step that occurs or is carried out during at least a portion of a medical procedure. Intraoperative, as defined herein, is not limited to surgical procedures, and may refer to other types of medical procedures, such as diagnostic and therapeutic procedures.

In various example embodiments of the present disclosure, systems and methods are disclosed whereby polarization-sensitive optical coherence tomography (PS-OCT) imaging is performed for the detection of anisotropic structure within a tissue region and employed for surgical guidance. Before describing further aspects of these embodiments, the present section of the disclosure provides illustrative examples of PS-OCT systems that may be employed within the systems and methods disclosed herein.

Polarization-sensitive optical coherence tomography (PS-OCT) is an alternate image modality to MRI, in which structural images can be obtained using light waves (i.e., optical) instead of magnetic waves. PS-OCT has been shown, for example, to be effective in finding the fiber tracts based on the degree of organization of the sample.

OCT is a technique for obtaining sub-surface images of translucent or opaque materials at a resolution equivalent to a low-power microscope. OCT is useful because it provides tissue morphology imagery at much higher resolution (better than 10 µm) than other imaging modalities such as MRI or ultrasound. OCT can be effectively viewed as an 'optical ultrasound', imaging reflections from within tissue to provide cross-sectional images.

OCT captures micrometer-resolution, three-dimensional images from within optical scattering media (e.g., biological tissue). OCT is an interferometric technique, typically employing near-infrared light. The use of relatively long wavelength light allows it to penetrate into the scattering medium. Confocal microscopy, another optical technique, typically penetrates less deeply into the sample but with higher resolution.

PS-OCT may be used to specifically visualize tissue exhibiting structural organization. Examples of such tissue structures include tendons that are attached to bones. Other examples of tissue that exhibit structural organization include ligaments, muscle, cartilage, tissue connective membrane, nerves, retina, blood vessel walls, some bone structures, trachea, esophagus, tongue and teeth.

Polarization sensitive OCT (PS-OCT) is a subset of OCT that can detect light intensity reflected from the sample at different polarization states. PS-OCT commonly generates a heat map or pseudo colored image (reference: "Correlation of collagen organization with polarization sensitive imaging of in vitro cartilage: implications for osteoarthritis," W. Drexler et. al, The Journal of Rheumatology, Vol. 28, No. 6, 1311-1318) where tissue structures with high degree of structural organization appear highlighted. PS-OCT systems can be used in orthopedic surgery to visualize tendons and optionally avoid unintentional damage to this tissue during a procedure. These identified regions of tissue exhibiting high level of structural organization (e.g. tendons and ligaments that are often located near skeletal structure) may be used in conjunction with a priori information, such as known points of attachment of tendons to bones, to geometrically correlate PS-OCT images to CT and MR images where bones are easily imaged.

In another example, PSOCT can help identifying nerve fiber bundles to help guide tumour resection. In many cases, brain tumours are grown around nerve fibers and the goal of resecting as much of the tumour as possible (i.e. to increase survival rate) while minimizing the damage to the nerve fibers (i.e. to reduce functional damages to the patient) remains very challenging when contrast between the tumour and nerve fibers are minimal in white light images. Identifying nerve fibers intraoperatively usually involve keeping the patient awake and receiving the patent's functional responses as the area identified, usually using pre-operative images and navigation system, is stimulated. As nerve fibers exhibit structural organization from its aligned fibers and the aligned protein and lipid in the fibers' myelin sheath, they provide a contrast in PSOCT images from other non-organized tissue such as grey matter as well as tumour grown in grey matter.

FIG. 1A illustrates an example implementation of a PS-OCT system 100. A computer controlled frequency sweeping laser source 102 (i.e. swept source laser) outputs a light beam. This light beam passes through a polarizer 104 to create a linearly polarized light which subsequently passes through a non-polarizing beam splitter 106 that splits the power of the input light equally into two arms—a reference arm at the bottom and a sample arm to the right.

The light in the sample arm passes through a quarter wave plate 108 at 45 degrees which modifies the polarization state of the light, such that the beam is incident onto a tissue surface of a subject 110 in a circular polarization state. This circularly polarized light may be scanned across a region in the sample to generate an image through a set of scanning mirrors 112 or galvanometers that are computer controlled through motor controllers 114. Light reflected and scattered back from the tissue region 110 is collected and is returned through the quarter wave plate 108 and coupled into two orthongonally polarized channels, towards the non-polarizing beam splitter 106.

The light in the reference arm reflects back to the non-polarizing beam splitter 106 after passing through several optical components. In the example embodiment shown, these components include a quarter wave plate 116 at 22.5 degrees, a dispersion compensation unit 118, an iris 120, and a neutral density filter 122, and mirror 124. The quarter wave plate 116 splits the reference arm power equally between the two orthongonally polarized channels while the dispersion compensation unit 118, iris 120 and neutral density filter 122 are configured to maximize the signal-to-noise and resolution of the interferometric signal.

The non-polarizing beam splitter 106 then combines the reflected reference light beam and the reflected and back-scattered sample light beam. The combined interferometric beam is then directed to another non-polarizing beam splitter 130 that splits the power equally into two orthongonal directions. Each of the split beams is directed through a respective polarizing beam splitter (132, 134) that splits the interferometric signal into two othogonal polarization channels. The same polarization channels from the two polarizing beam splitters (132, 134) then propagate to respective balanced detectors (142, 144) for converting the interferometric signals into electrical signals. These electrical signals then converts to a digital signal through a Data Acquisition card 150 (DAQ) which then are stored and processed in the connected computer 155 to generate PS-OCT images.

Figure 1B:
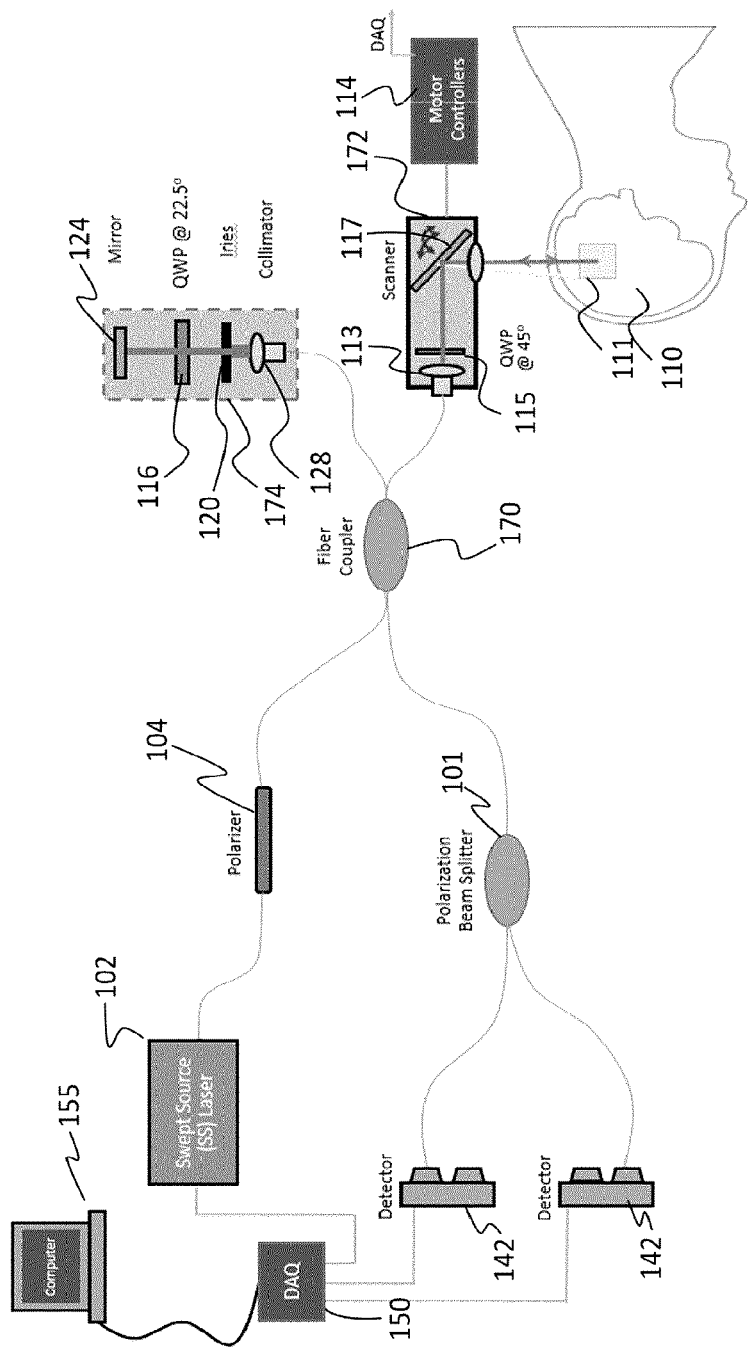
FIG. 1B illustrates an example embodiment of a fiber-based PS-OCT system.

FIG. 1B illustrates an example embodiment of a fiber based PS-OCT system using a frequency sweeping laser source 102 (i.e. swept source laser). The light beam from the swept source passes through a polarizer 104 to create a linearly polarized light which subsequently passes through a fiber coupler 170 that splits the power of the input light equally into two arms—a reference arm 174 and a sample arm 172. The light in the sample arm passes through a scanner incorporating a collimater 113 to collimate the light output from the fiber, a quarter wave plate 115 at 45 degrees which sets the light to a circular polarization state going into the tissue sample. This circularly polarized light can scan across a region 111 in the sample 110 to generate an image through a set of scanning mirrors or galvanometers 117 that are computer controlled through motor controllers 114. Light reflected and scattered back from the tissue sample goes back through the quarter wave plate and is coupled into two orthongonally polarized channels towards the fiber coupler 170.

Similar to the sample arm, the light entering the reference arm reflects back to the fiber coupler after passing through a similar arrangement of optical components the main difference being that in the case of the reference arm the final element from which the reflected signal is generated is a mirror element 124 as opposed to the sample 110 such as that in the sample arm. The components in the reference arm similar to the sample arm include a collimator 128 and a quarter wave plate 116 at 22.5 degrees in addition the reference arm also includes an iris 120. The quarter wave plate splits the reference arm power equally between the two orthongonally polarized channels while the iris maximizes the signal-to-noise and resolution of the interferometric signal.

After both signals from the reference and sample arm are generated, the fiber coupler then interferes the reflected reference light beam signal and the reflected sample light beam signal, and the interfered beams propage to a polarizing beam splitter 101 that separates the now interfered light signals into two orthongonal polarization states. Each of the split-polarized signals are channeled their respective detectors 142 for conversion from interferometric optical signals into electrical signals. The electrical signals are then subsequently converted into digital signals through a Data Acquisition card (DAQ) 150 which are then stored and processed in the connected computer 155 to generate PSOCT images.

It is important to note that the quarter waveplates in the reference and sample arm are switchable with polarization controller or polarization modulator to module the light polarization into other states for tissue imaging.

Figure 2:
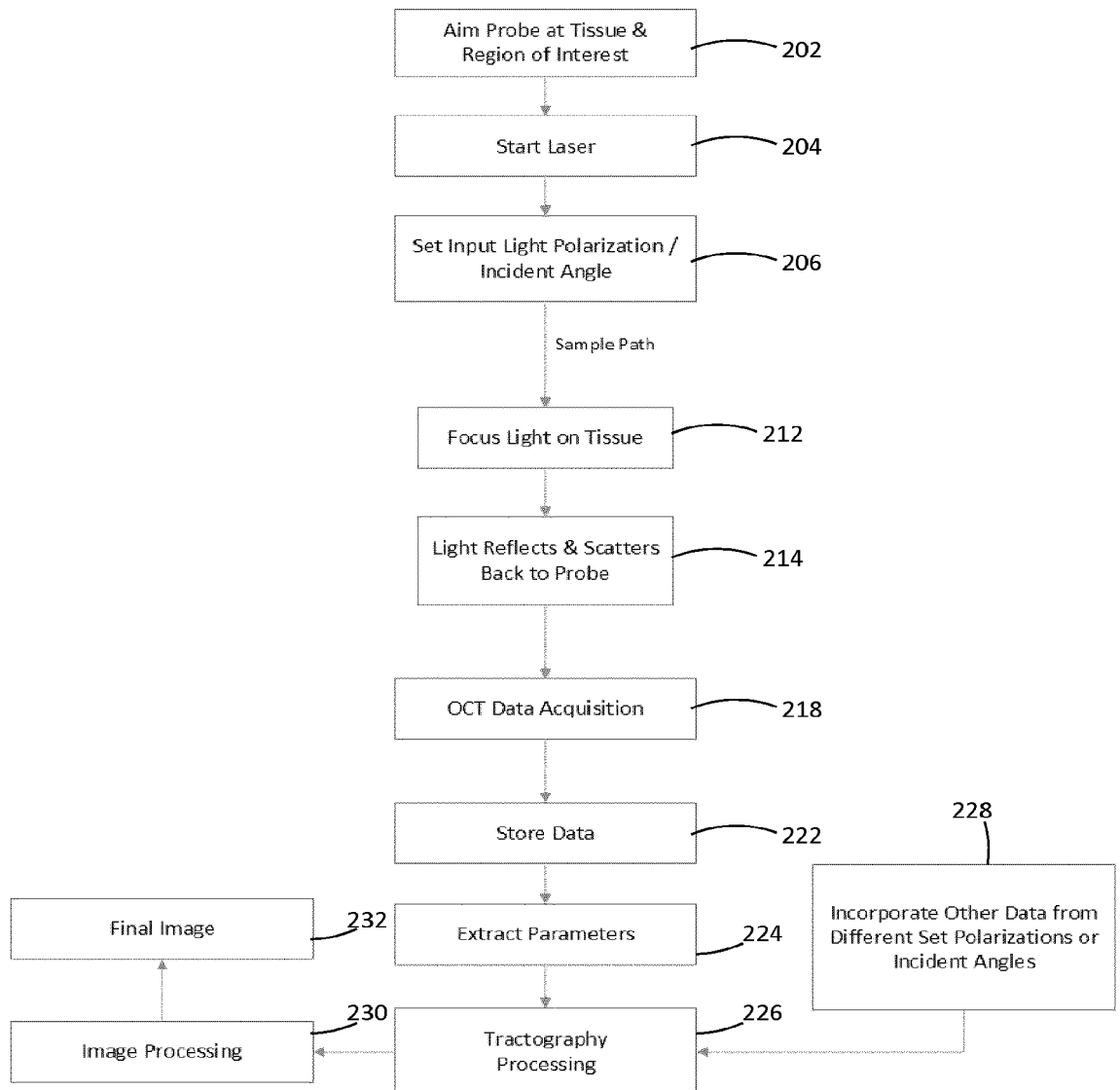
FIG. 2 illustrates an example process of PS-OCT image acquisition.

Referring now to FIG. 2, a flow chart is provided that illustrates an example process of PS-OCT image acquisition. The process begins at step 202 with aiming a probe at the region of interest of the tissue being imaged. The light source (or laser) is turned on at step 204 and light polarization state and incident angle are set 206 for generating light reflection and scattering from the tissue region being focused on. When executing this step there may be one or more polarization states that could be set to probe the sample as will be elaborated further as follows.

For example, in one embodiment, a circular polarization state may be used to probe the sample. More specifically, when interrogating brain tissue, a circular polarization enables fiber tracts or bundles lying on the plane perpendicular to the light beam to be visualized. In another example embodiment, multiple linearly polarized light at different azimuth angles may be used to interrogate the sample. In the aforementioned example of measuring brain tissue, each of these linearly polarized light beams could be focused to probe fiber tract or bundle directionality in a particular azimuth angle. In a subsequent embodiment, two orthongonal elliptically polarized light beams could also be used to determine fiber tract and bundles orientation lying on the plane perpendicular to the light beam. In yet another embodiment multiple incident angles at different altitudes could also be set to obtain orientations that are in or near the direction of the light propagation.

Continuing with the flow chart depicted in FIG. 2, in step 212, the light is propagated towards the tissue where it interrogates the tissue and is scattered or reflected back to the probe as per step 214. Subsequently in step 218, the detector then detects the electrical signal output from the probe and is converted into a digital format that is then stored, for example, in a computer hard drive or memory as per step 222. In certain instances, the probe depth or position may be shifted during the acquisition, in which compensatory readjustment of the probe or the reference light path may be applied as is known in the art.

After storing the data at step 222, parameter extraction occurs at step 224 to extract parameters such as stokes parameters, degree of polarization, intensity, retardance, and/or orientation data from the interferometric signal. Each of these parameters provide different optical properties of the tissue being imaged.

An example process in data extraction from the detector is described in "Polarization maintaining fiber based ultra-high resolution spectral domain polarization sensitive optical coherence tomography," Gotzinger, et. al, Opt. Express, 2009, December; 17(25): 22704-22717. In general, the detected interference signal (i.e. also called the spectral fringe) represents the amount of light reflection from the sample in each temporal frequency. The higher frequencies of the spectral fringe correspond to deeper reflectors in the sample. To reconstruct the spectral fringe into reflectivity in spatial domain, the fringe data need to rescale from the temporal frequency (k) into spatial frequency (k) with the relation (k=2πf/c) where c is the speed of light, as depth information are a Fourier pair with wavenumber-indexed spectra. After rescaling, a fast Fourier transform (FFT) is applied to convert the data into spatial depth reflectivity. This is done for every A-scan to form a 2D intensity map and a 3D Volumatic.

Before rescaling and FFT, one or more additional processes may be applied to remove some artifacts such as fixed pattern noise or camera artefacts. These artefacts are noise or intensity patterns that are either consistent throughout the spectrum or consistent for every scan which can be removed by a subtracting a mean spectrum or a reference spectrum respectively.

Dispersion could also be introduced as spectral fringe is chirped in the signal propagation and conversion process which results in a poorer resolution. This can be compensated in data as well. The publication Wojtkowski M, Srinivasan V, Ko T, Fujimoto J, Kowalczyk A, Duker J. Ultrahigh-resolution, high-speed, Fourier domain optical coherence tomography and methods for dispersion compensation. Opt. Express. 2004; 12(11):2404-2422 described one example on compensating dispersion.

After FFT, the different OCT images of reflectivity, retardation (showing strength of organization, and orientation (showing direction of organization) can be generated using equations described by Hitzenberger C K, Goetzinger E, Sticker M, Pircher M, Fercher A F. Measurement and imaging of birefringence and optic axis orientation by phase resolved polarization sensitive optical coherence tomography. Opt. Express. 2001; 9(13):780-790. The equations are as follows:

$$R(z) = I_1(z)^2 + I_2(z)^2 \text{ Reflectivity}$$

$$\delta(z) = \tan^{-1}\left(\frac{I_2(z)}{I_1(z)}\right) \text{ Retardation}$$

$$\theta = \frac{180° - \varphi_1 + \varphi_2}{2} \text{ Orientation}$$

where $I_x$ and φ are the intensity and phase from each polarization channel from each detector.

Since retardation and orientation provide magnitude and direction of tissue organization respectively, these two parameters can be combined to form optical tractography maps. Optical tractography maps may comprise an array of voxels further containing tensors having magnitude and direction which may mimic white matter tracts. To form a tractography map using PSOCT data, retardation and orientation values are used as the equivalents of magnitude and direction of tensor measurement data acquired using MRI. However, in some examples PSOCT devices may only detect white matter fiber tracts in a direction normal to the interrogating light beam thus the resulting white matter tracts would only have a direction defined in the plane normal to the interrogation beam.

Therefore in such a case, the steps of generating a tractography map involve first determining the plane perpendicular to the incident of the laser light. This can be achieve through a calibrated navigation system where the OCT scanner position and its preset laser direction are obtained to determine the angle of the perpendicular plane in 3D space. Then within the plane, the fiber tract is identify through the local retardation value obtained in PSOCT imaging. White matter is more organized tissue in which higher retardation value is obtained compared to grey matter. A threshold can be set to determine the boundary between white matter tracts and grey matter. Once the tract location is identified on the array of tensors, the direction of these tensors are then obtained through the local orientation values in the PSOCT images.

Finally the tractography of the white matter tracts can then be obtained through the array of tensor maps determined with respect to the predetermined location of the plane from navigation system and tracking probe attached to the OCT scanner. In another example, instead of retardation information from OCT, intensity information can also be used to determine the boundary between white matter tracts and grey matter. White matter reflects more and scatters less into the tissue than grey matter. By determine the rate of reflectivity change into the tissue in reflectivity images in OCT, the white matter tract can be segmented out using a preset threshold value. A combination of retardation and intensity data could also be used where the preset threshold for segmentation is set using both retardation and intensity data to improve accuracy.

Once the parameter extraction step is completed, the parameters are processed at step 226 to generate image data characterizing the anisotropic structure within the tissue volume that was imaged. This processing occurs using one or multiple data from different set polarization states and/or incident angles. It is important to note that even though OCT images are typically only a few centimeters by a few centimeters, a larger tractography map can be generated through stitching multiple OCT images together with offsets provided by a navigation system with tracking system attached to the OCT scanner and or an automatic positioning system.

Figure 3A:
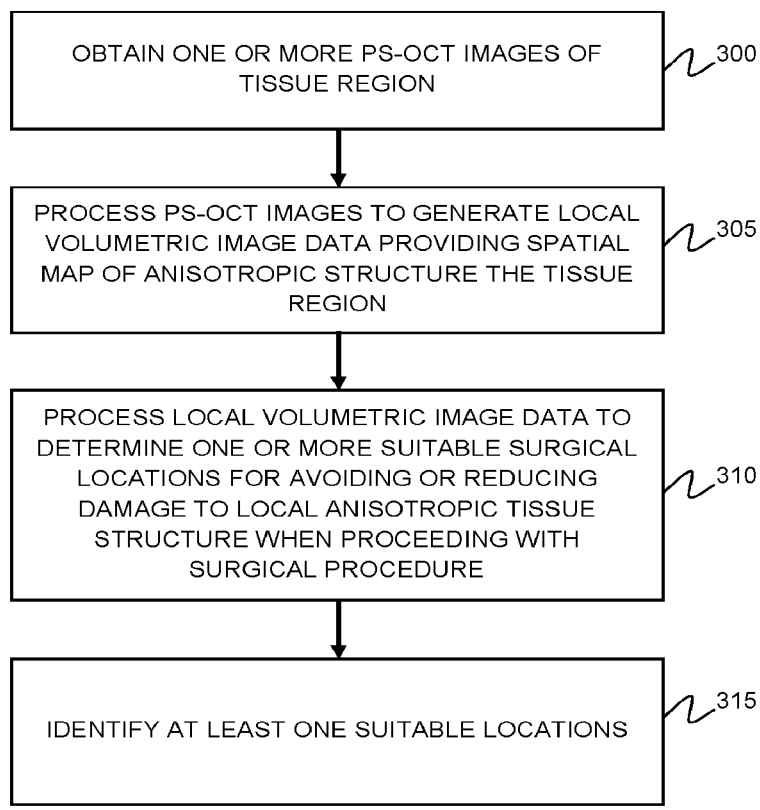
FIG. 3A is a flow chart illustrating an example method of identifying a suitable location for proceeding with a surgical procedure based on the detection of anisotropic tissue structure via PS-OCT.

In one example embodiment, PS-OCT image data is employed for the characterization of anisotropic tissue structure within a tissue region, and the anisotropic tissue structure is employed to identify a suitable surgical location for proceeding with a surgical procedure, such that anisotropic structure within the tissue region is avoided, or such that damage to the anisotropic structure is reduced or minimized. FIG. 3A provides a flow chart illustrating an example implementation of such a method. In step 300, one or more PS-OCT images are obtained from a tissue region. The PS-OCT images may comprise PS-OCT image data acquired from a tissue region below a tissue surface, optionally including the surface itself.

The tissue surface may be an externally exposed tissue surface, or may be an internal surface that is accessible, for example, by the at least partial insertion of a PS-OCT probe into a subject. The tissue region is a local tissue region, due to the local nature of the PS-OCT measurement, which probes a volume residing below a surface, proximal to the surface, typically with a depth less than 3 mm. It will be understood that the volume of tissue probed will depend on a number of factors, including, but not limited to, the wavelength of the OCT light, the intensity of the OCT light, and the scattering and absorbing properties of the tissue being probed.

Once a local tractography map is generated from OCT images, a surgeon or a physician has obtained an intraoperative tractography map of the region of interest (i.e. a few centimeters by a few centimeters or smaller) in the surgical field containing information related to the spatial orientation of white matter tracts within the region.

In some embodiments this process of local tractography map generation may be repeated on adjacent regions until enough local tractography maps are generated such that the actual location of all the white matter tracts around or within a planned entry area are visible. This may enable the surgeon to reconsider the chosen entry point in lieu of one that avoids or reduces damage to the local anisotropic tissue structures such as white matter tracts. This information may also be compared with pre-operative images such as an MRDTI scan spatially registered to the patient to identify and confirm any eminent tracts that are at risk. In addition, any significant deviation between the spatial location of the tractography information acquired using the OCT probe and the spatial location of similar structures in the MRDTI scan acquired via the navigation system may be used to adjust the registration. Once an entry point is chosen the surgeon may proceed with the surgical procedure.

In some embodiments, the above procedure may be automated using a processor. For example white matter tracts generally have a very organized structure that may be quantified by PSOCT retardance values, as retardance is proportional to the degree of organization of an imaged tissue. Given that generally white matter is a tissue having a high degree of organization, higher retardation values are usually obtained when imaging it in comparison to commonly found adjacent tissue structures such as grey matter. Thus using this knowledge a threshold retardance value may be set to differentiate between highly organized tissue and non-organized tissue and in some embodiments determine the boundary between highly organized tissue and non-organized tissue where higher organization correlates with white matter and non-organization correlates with grey matter. For example, once an OCT scan of a volume is taken a processor may analyze the voxels in the image to compute whether they have a retardance value lower or higher than the set threshold and tag them accordingly. This tagging may be subsequently mapped to the PSOCT volume image and used to augment its visualization to communicate suggested regions where entry would be most suitable to reduce trauma to the patient. For example voxels tagged with a higher retardance value than the threshold may be colored red indicative of areas where there is a higher probability of penetrating white matter upon penetration of the tissue for entry, while voxels with a lower threshold may be colored white indicative of areas where there is a lesser probability of penetrating white matter upon penetration of the tissue for entry.

In another example embodiment, the retardance values of all the voxels in the scanned volume of the PSOCT scan may be processed as an average and instead of a visualization of the scan, the processor may provide a "suitable" or "not suitable" reading indicating whether the average value was above a threshold or not and thus whether the location is suitable for entry into the tissue or not. It should be noted that various computations employing the metrics acquired by any applicable PSOCT system may be used to indicate a suitable result to a surgeon, and thus the embodiments described above are not meant to limit the scope of the system described herein.

Finally, in step 315, output is provided for communicating the location of at least one of the suitable surgical locations. For example, the output may be displayed on a display device that can be viewed by a user, operator, or clinician. Alternatively, the output can be provided to a surgical robotic system, for the automated selection of a suitable surgical location for proceeding with an automated surgical procedure.

In example implementations in which the suitable surgical location is displayed on a display device, the at least one surgical location may be identified on a displayed image that is generated, at least in part, based on pre-operative image data. This may be achieved, for example, for cases in which the tissue region is identifiable in a patient reference frame to which the pre-operative image data is referenced, allowing for one or more annotations of the image, where each annotation identifies the location, within the image, corresponding a given suitable surgical location. For example, if the PS-OCT measurements are made by a PS-OCT probe that has fiducial markers provided thereon, the position and orientation of the probe may be tracked relative to a global reference frame that can be referenced to a patient reference frame, thereby allowing the tissue region to be located within the patient reference frame. In some embodiments, the displayed image may be based on both pre-operative image data, and based on the local volumetric image data that shows the local anisotropic structure detected via PS-OCT.

In one example implementation, the pre-operative volumetric image data is obtained from diffusion tensor imaging data. Currently, various magnetic resonance imaging (MRI) techniques are employed to generate tractography information of the brain. One such technique is known as diffusion tensor imaging (DTI). Diffusion tensor imaging (DTI) is a MRI technique that measures macroscopic axonal organization in nervous system tissues. Diffusion tensor imaging (DTI) enables the measurement of the restricted diffusion of water in tissue in order to produce neural tract images instead of using this data solely for the purpose of assigning contrast or colors to pixels in a cross sectional image. It also provides useful structural information about muscle and tissue.

In DTI, each voxel has one or more pairs of parameters: a rate of diffusion and a preferred direction of diffusion—described in terms of three-dimensional space—for which that parameter is valid. The properties of each voxel of a single DTI image are usually calculated by vector or tensor mathematical operations from six or more different diffusion weighted acquisitions, each obtained with a different orientation of the diffusion sensitizing gradients. In some methods, hundreds of measurements—each making up a complete image—are made to generate a single resulting calculated image data set. The higher information content of a DTI voxel makes it extremely sensitive to subtle pathology in the brain. In addition the directional information can be exploited at a higher level of structure to select and follow neural tracts through the brain.

It will be understood that the local anisotropic tissue structures characterized by the local volumetric image data will depend on the type of tissue that is imaged. Non-limiting examples of the anisotropic tissue structures that may be characterized by the local volumetric image data include nerve tissue structure, spinal tissue structure, muscle tissue structure, tendon tissue structure, and ligament tissue structure. In another example implementation, the anisotropic tissue structures may be one or more anisotropic tissue structures of ocular tissue.

As described in detail below, in some example embodiments, the tissue may be brain tissue, and the local anisotropic tissue structure may characterize fiber tracts, such that the displayed image includes tractography information. In cases in which the displayed image is generated, at least in part, by pre-operative image data, the pre-operative image data may include pre-operative tractography information, and may also include local tractography information determined based on the local volumetric image data.

In some example embodiments, the local volumetric image data may be spatially registered to pre-operative volumetric image data, where the pre-operative volumetric image data identifies anisotropic tissue structures within a tissue region that is larger than, and includes, the tissue region imaged by PS-OCT. The local volumetric image data may then be registered to the pre-operative volumetric image data, for example, using known registration methods such as, but not limited to, one described in Wang et al., 'Cross-validation of serial optical coherence scanning and diffusion tensor imaging: A study on neural fiber maps in human medulla oblongata,' NeuroImage 100 (2014) 395-404.

In general, the co-registration involves two steps: (1) performing image registration to align the DTI to the optical images, and (2) applying the rotational component of this registration to the orientation vectors derived from diffusion MRI to map them to the coordinate system of the optical images.

In one example implementation, the local volumetric image data was registered to the pre-operative volumetric image data using the method described in the aforementioned publication. The DTI dataset was first mapped into the optical imaging space and interpolated to match the voxel size of optical image. Then, a rigid transformation (translation and rotation) followed by an affine alignment (translation, rotation, scaling and shearing) was estimated and applied to the Functional Anisotropy block using a modification of the symmetric registration procedure described in Reuter et al. (Highly accurate inverse consistent registration: a robust approach. NeuroImage (2010) 53, 1181-1196) with normalized mutual information as the cost function.

After spatial alignment, the DTI orientation vectors were reoriented to map onto optical image coordinates. Vector reorientation was performed using the transformation that was obtained with the image registration procedure described above. First, the registration was applied to the tensor volumes to map them to the coordinate space of the orientation images. Second, the rotation matrix extracted from the registration transform was applied to reorient the tensors. The primary eigenvectors were extracted from the registered diffusion tensor maps. Because the optic axis orientation is defined on the xy-plane, the DTI vectors were projected onto the end-face plane of the optical image.

Common methods for multi-modal image registration above include those described in "Multi-modal image registration for pre-operative planning and image guided neurosurgical procedures," Risholm, et. al, Neurosurg Clin N Am, 2011, April; 22(2): 197-206 and "Image registration of ex-vivo MRI to sparsely sectioned histology of hippocampal and neocortical temporal lobe specimens," Goubran et. al, NeuroImage, 83 (2013); 770-781. Broad classes of image registration methods for medical images is also described in detail in "A survey of medical image registration," Maintz et. al, Medical Image Analysis (1998), Vol. 2, No. 1, pp: 1-36.

Having spatially registered the local volumetric image data to the pre-operative volumetric image data, the co-registered image data may be processed to determine, for at least one of the suitable surgical locations, one or more suitable surgical trajectories for avoiding or reducing damage to local anisotropic tissue structure residing within the first tissue region and the second tissue region. In an example embodiment this may be accomplished by a processor by first deriving suitable entry points from the spatially registered PSOCT scan such as by methods described above. Once the processor has mapped the suitable entry points onto the registered PSOCT scan it may further map these areas onto the preoperative volumetric image data. From this an array of trajectories may be created by extending a trajectory from each of the suitable entry points to the planned target (determined prior to surgery) and visualized. These trajectories may then be visualized on the guidance software via the processor and presented to the user for selection.

For example, to form a tractography map using PSOCT data, retardation and orientation values are used as the magnitude and direction of an array of tensors. However, in embodiments where PSOCT detects fibers tracts on a plane substantially normal to the incident of the laser light, a planar tractography map may be produced.

In such an embodiment, the steps involved in forming a tractography map are as follows. Initially determining the plane perpendicular to the incident of the laser light. This can be achieve through a calibrated navigation system where the OCT scanner position and its preset laser direction are obtained to determine the angle of the perpendicular plane in 3D space. Then, within the plane, the fiber tract is identified through the local retardation values obtained during PSOCT imaging. White matter is more organized tissue in which higher retardation value is obtained compared to grey matter. A threshold can be set to determine the boundary between white matter tracts and grey matter. Once the tract location is identified on the array of tensors, the direction of these tensors are then obtained through the local orientation values in the PSOCT images.

Finally the tractography of the white matter tracts can then be obtained through the array of tensor maps generated with respect to the predetermined location of the plane from the navigation system and corresponding tracking probe attached to the OCT scanner. In another example, instead of retardation information from OCT, intensity information can also be used to determine the boundary between white matter tracts and grey matter. White matter reflects more and scatters less into the tissue than grey matter. By determining the rate of reflectivity change within the tissue through analyses of reflectivity images acquired using OCT, the white matter tracts may be segmented out using a preset threshold value. A combination of retardation and intensity data could also be used where the preset threshold for segmentation is set using both retardation and intensity data to improve accuracy.

At least one suitable surgical trajectory may then be displayed on a display device that can be viewed by a user, operator, or clinician. Alternatively, the output can be provided to a surgical robotic system, for the automated selection of a suitable surgical location for proceeding with an automated surgical procedure.

In one example embodiment, the at least one suitable surgical location and the at least one suitable surgical trajectory may be identified on a displayed image that is generated based on pre-operative image data.

In another example embodiment, one or more entry points may be selected, by an operator, from the one or more suitable surgical locations, and a suitable surgical trajectory may be identified on the display device for each selected entry point.

Figure 3B:
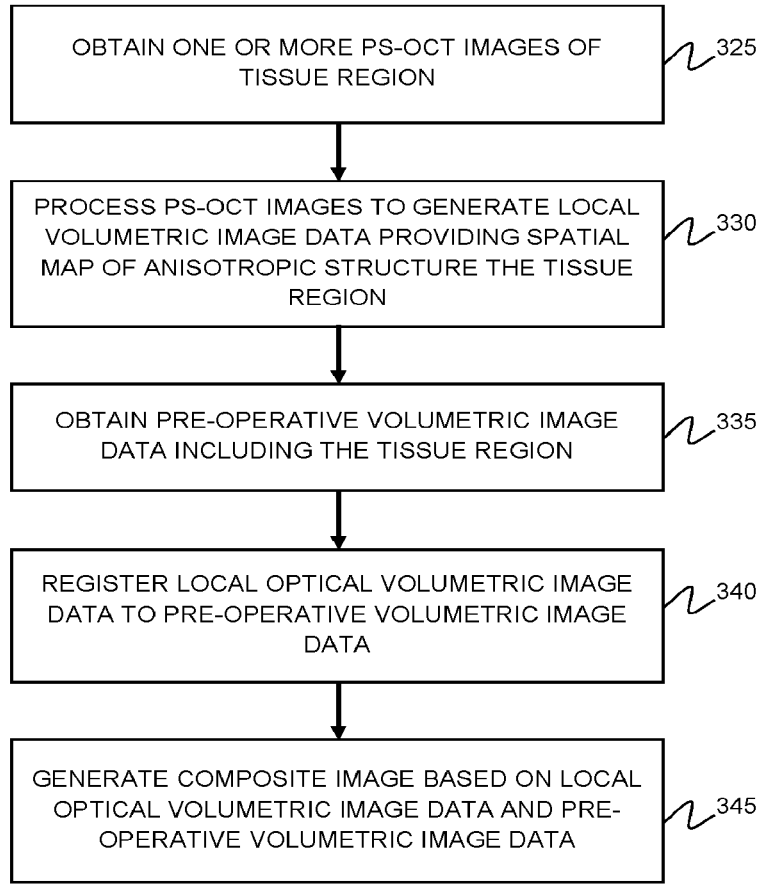
FIG. 3B is a flow chart illustrating an example method of generating a composite image including pre-operative volumetric image data and local volumetric image data characterizing anisotropic structure detected via PS-OCT.

FIG. 3B is a flow chart illustrating another example embodiment in which the local volumetric image data, characterizing the anisotropic structure in the tissue region, is co-registered with pre-operative image data, such that a composite image may be generated and displayed on a display device. In step 325, one or more PS-OCT images are obtained. The PS-OCT images are processed in step 330 to generate local optical volumetric image data associated with the tissue region, the local optical volumetric image data providing a spatial map of anisotropic structure within the tissue region. In step 335, pre-operative volumetric image data, including the tissue region, is obtained. In step 340, the local optical volumetric image data is then registered to the pre-operative volumetric image data, for example, using the example methods described above.

A composite image is then generated based on the local optical volumetric image data and the pre-operative volumetric image data, as shown at step 345, and the composite image may be presented on a display device.

Figure 3C:
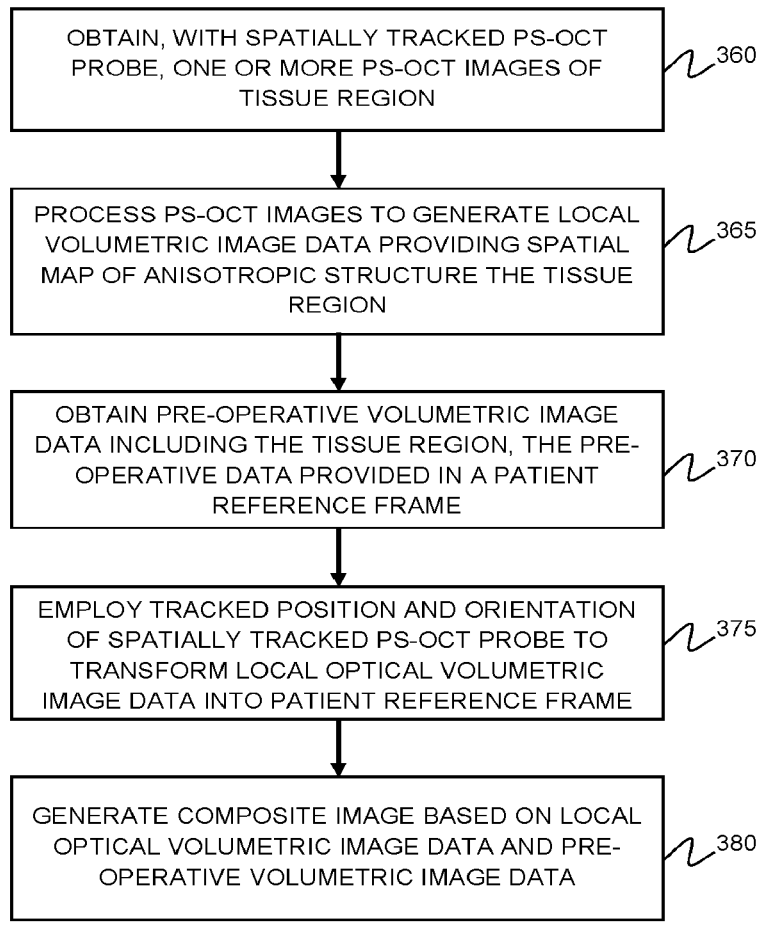
FIG. 3C is a flow chart illustrating an alternative example method of generating a composite image including pre-operative volumetric image data and local volumetric image data characterizing anisotropic structure detected via PS-OCT.

In the example method illustrated in FIG. 3B, a composite image is generated based on registration of the local volumetric image data with the pre-operative image data. In the alternative example embodiment shown in FIG. 3C, the composite image is generated based on the tracking of a PS-OCT probe. In step 360, one or more PS-OCT images of a tissue region are obtained with a spatially tracked PS-OCT probe. The images are processed in step 365 to generate local optical volumetric image data associated with the tissue region, the local optical volumetric image data providing a spatial map of anisotropic structure residing within the tissue region. In step 370, pre-operative volumetric image data, including the tissue region, is obtained in a patient reference frame.

The tracked position and orientation of the spatially tracked PS-OCT probe is then employed in step 375 to transform the local optical volumetric image data into the patient reference frame. A composite image is generated in step 380 based on the local optical volumetric image data and the pre-operative volumetric image data, which may then be presenting the composite image on a display device.

In example implementations in which the anisotropic tissue structures are tendons or ligaments, the spatial registration of detected anisotropic structures with pre-operative images involving bone structures may be performed by employing insertion sites, tendon-bone junctions and ligament-bone junctions, known as enthuses. The anatomical locations of entheses are well known and landmarks can be identified on the bone in the vicinity of these attachment points (reference: "Anatomy and biochemistry of enthuses," Michael Benjamin, Ann Rheum Dis 2000, Vol. 59, Issue 12, pg. 995-999). Hence, this a priori anatomical information about the position of the tendon or ligament relative to bone structures in the vicinity can be used to register intraoperative PS-OCT image of the tendons or ligaments with pre-operative images obtained using other modalities that accurately image the bone structures. For example, the tendon-bone junction in the Achilles tendon enthesis is immediately proximal to the superior tuberosity. This region is characterized by a highly irregular interface at the attachment points or junction. This characteristic structure of the bone can be used to identify the junction where the tendon attaches to the bone. The geometric correlation of images that are thus obtained using different modalities, and often at different scales, is known as image registration or image fusion.

Figure 4:
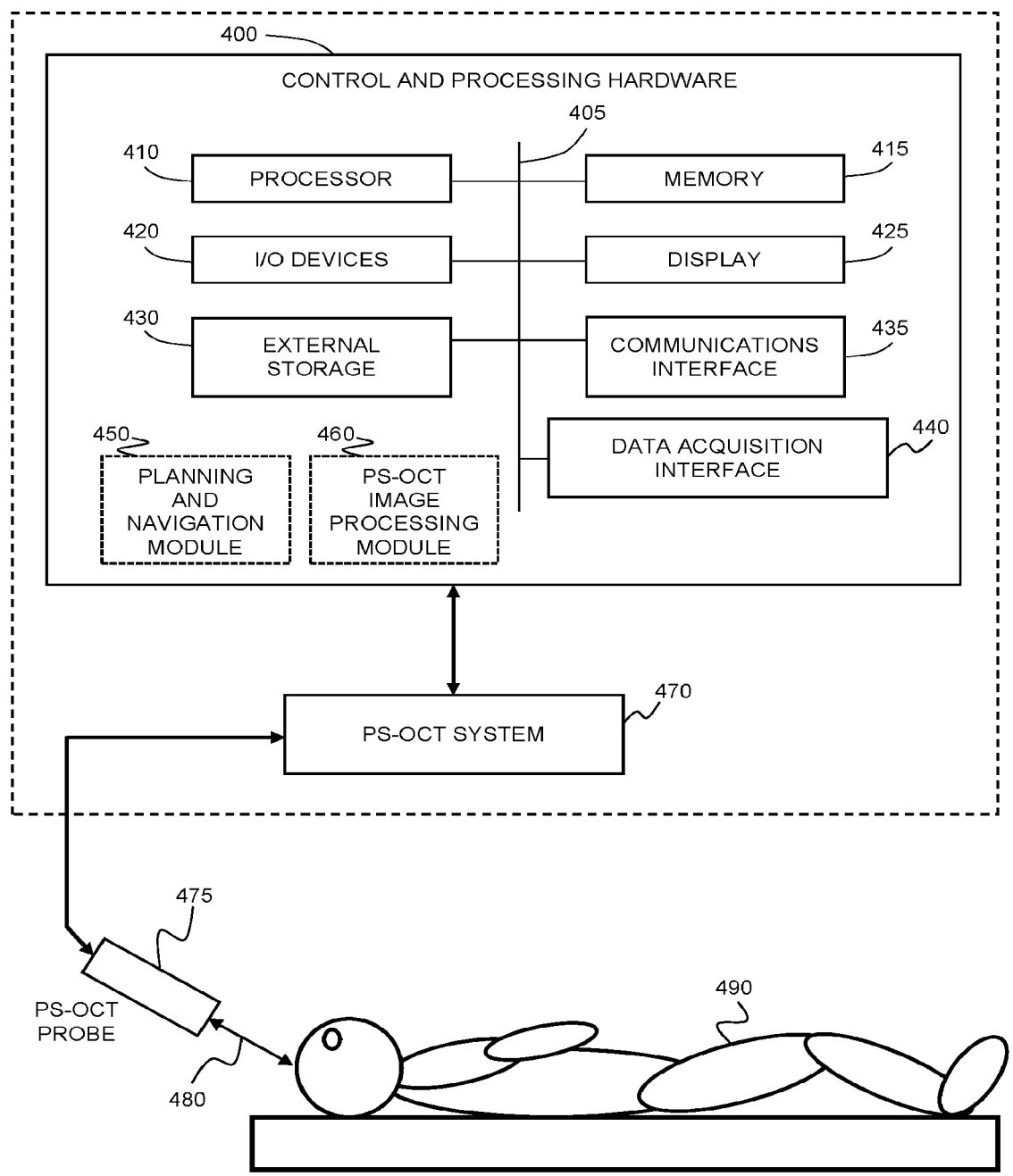
FIG. 4 illustrates an example system for performing surgical guidance based on the detection of anisotropic tissue structures via PS-OCT.

Referring now to FIG. 4, an example system is shown for performing capacitive position monitoring during a medical procedure. The example system includes a PS-OCT probe 475 that is operatively coupled to a PS-OCT system 470. PS-OCT probe 475 and system 470 may be based, for example, the example PS-OCT systems shown in FIG. 1A and FIG. 1B, where on or more of the distalmost optical components are housed within the PS-OCT probe 470. During use, the PS-OCT probe is placed in close proximity to the subject for interrogating a tissue region.

Although the figure shows the optical interrogation of a tissue region below an external tissue surface, in which the distal portion of the PS-OCT probe positioned outside of the body of the subject, in other embodiments the probe may be at least partially inserted into the subject's body for the analysis of an internal tissue region.

As shown in the example embodiment illustrated in FIG. 4, control and processing hardware 400 may include a processor 410, a memory 415, a system bus 405, one or more input/output devices 420, and a plurality of optional additional devices such as communications interface 435, display 425, external storage 430, and data acquisition interface 440.

The present example methods of performing PS-OCT based tissue analysis and surgical guidance can be implemented via processor 410 and/or memory 415. As shown in FIG. 4, the volumetric image data characterizing the anisotropy in a tissue region imaged by the PS-OCT probe 475 is calculated by control and processing hardware 400, via executable instructions represented as PS-OCT image processing module 460. The control and processing hardware 400 may include and execute instructions for planning and navigation of a surgical procedure, and for modifying and/or validating a navigated procedure based on anisotropic structure detected within a tissue region.

The methods described herein can be partially implemented via hardware logic in processor 410 and partially using the instructions stored in memory 415. Some embodiments may be implemented using processor 410 without additional instructions stored in memory 415. Some embodiments are implemented using the instructions stored in memory 415 for execution by one or microprocessors. Thus, the disclosure is not limited to a specific configuration of hardware and/or software.

It is to be understood that the example system shown in the figure is not intended to be limited to the components that may be employed in a given implementation. For example, the system may include one or more additional processors. Furthermore, one or more components of control and processing hardware 400 may be provided as an external component that is interfaced to a processing device. For example, as shown in the figure, PS-OCT system 470 may be included as a component of control and processing hardware 400 (as shown within the dashed line), or may be provided as one or more external devices.

While some embodiments can be implemented in fully functioning computers and computer systems, various embodiments are capable of being distributed as a computing product in a variety of forms and are capable of being applied regardless of the particular type of machine or computer readable media used to actually effect the distribution.

At least some aspects disclosed herein can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

A computer readable storage medium can be used to store software and data which when executed by a data processing system causes the system to perform various methods. The executable software and data may be stored in various places including for example ROM, volatile RAM, nonvolatile memory and or cache. Portions of this software and/or data may be stored in any one of these storage devices. As used herein, the phrases "computer readable material" and "computer readable storage medium" refers to all computer-readable media, except for a transitory propagating signal per se.

Some embodiments of the present disclosure relate to minimally invasive medical procedures that are performed via an access port, whereby surgery, diagnostic imaging, therapy, or other medical procedures (e.g. minimally invasive medical procedures) are performed based on access to internal tissue through the access port.

An example of an access port is an intracranial access port which may be employed in neurological procedures in order to provide access to internal tissue pathologies, such as tumors. One example of an intracranial access port is the BrainPath surgical access port provided by NICO, which may be inserted into the brain via an obturator with an atraumatic tip in the brain. Such an access port may be employed during a surgical procedure, by inserting the access port, via the obturator that is received within the access port, through the white matter fibers of the brain to access a surgical site.

Figure 5:
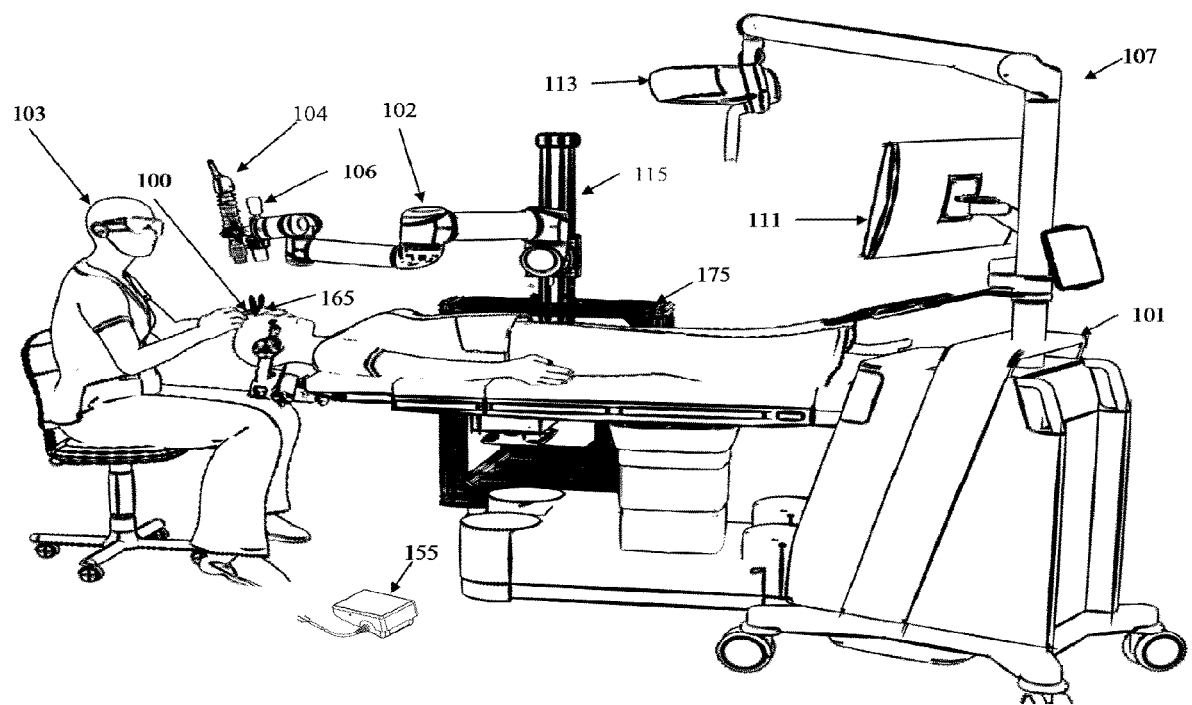
FIG. 5 is a diagram illustrating components of an example surgical system used in port based surgery.

FIG. 5 is a diagram illustrating components of an example surgical system used in port based surgery. FIG. 5 illustrates a navigation system 507 having an equipment tower 501, tracking system 513, display 511 (for a graphical user interface), an intelligent positioning system 575 and tracking markers 565 used to track medical instruments or an access port 500. Tracking system 513 may also be considered an optical tracking device or tracking camera.

In FIG. 5, a surgeon 503 is performing a tumor resection through a port 500, using an imaging device 504 to view down the port at a sufficient magnification to enable enhanced visibility of the instruments and tissues. The imaging device 504 may be an exoscope, videoscope, wide field camera, or an alternate image capturing device. The imaging sensor view is depicted on the visual display 511 which surgeon 503 uses for navigating the port's distal end through the anatomical region of interest. A foot pedal 555 is located in an accessible vicinity to the surgeons foot and is utilized to actuate an element used in the procedure.

The intelligent positioning system 575 receives as input the spatial position and pose data of the automated arm 502 and target (for example the port 500) as determined by tracking system 513 by detection of tracking markers 565. Active or passive fiduciary tracking markers 565 may be placed on the port 500 and/or imaging device 504, and/or any associated medical instruments, such as wide field camera 506, to determine the location of these objects using the tracking camera 513 and navigation system 507. These markers 565 may be reflective spheres configured to be seen by the stereo camera of the tracking system to provide identifiable points for tracking. A tracked instrument in the tracking system is typically defined by a grouping of markers 565, which identify a volume and any projected extensions thereof, and are used to determine the spatial position and pose of the volume of the tracked instrument in three dimensions. Typically, in known example tracking systems a minimum of three spheres are required on a tracked tool to define the instrument, however it is known in the art that the use of four markers 565 is preferred.

Figure 6A:
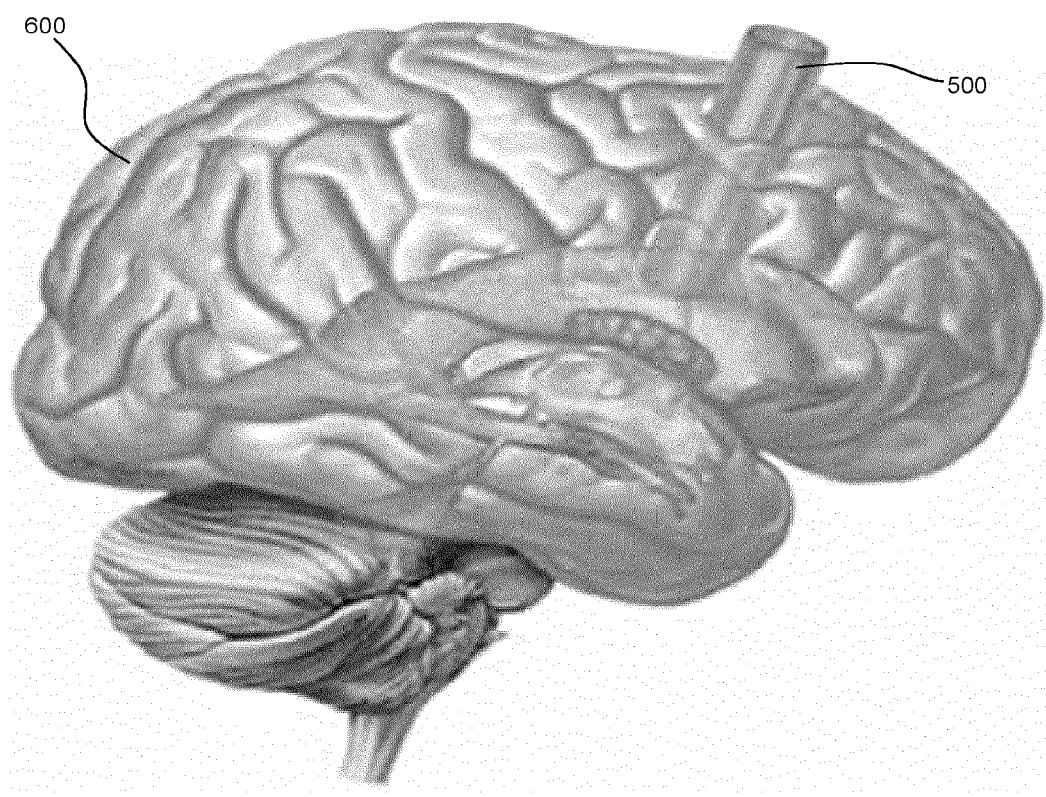
FIG. 6A illustrates the insertion of an access port into a human brain, for providing access to internal brain tissue during a medical procedure.

FIG. 6A illustrates the insertion of an access port into a human brain, for providing access to internal brain tissue during a medical procedure. In FIG. 6A, access port 500 inserted into a human brain 600, providing access to internal brain tissue. Surgical tools and instruments may then be inserted within the lumen of the access port in order to perform surgical, diagnostic or therapeutic procedures, such as resecting tumors as necessary.

As seen in FIG. 6A, access port 500 comprises of a cylindrical assembly formed of an outer sheath. Port 500 may accommodate an introducer (or probe) which is an internal cylinder that slidably engages the internal surface of port 500. The probe may have a distal end in the form of a conical atraumatic tip to allow for insertion into the sulcal folds of the brain. Port 500 has a sufficient diameter to enable bimanual manipulation of surgical tools within its annular volume such as suctioning devices, scissors, scalpels, and cutting devices.

Figure 6B:
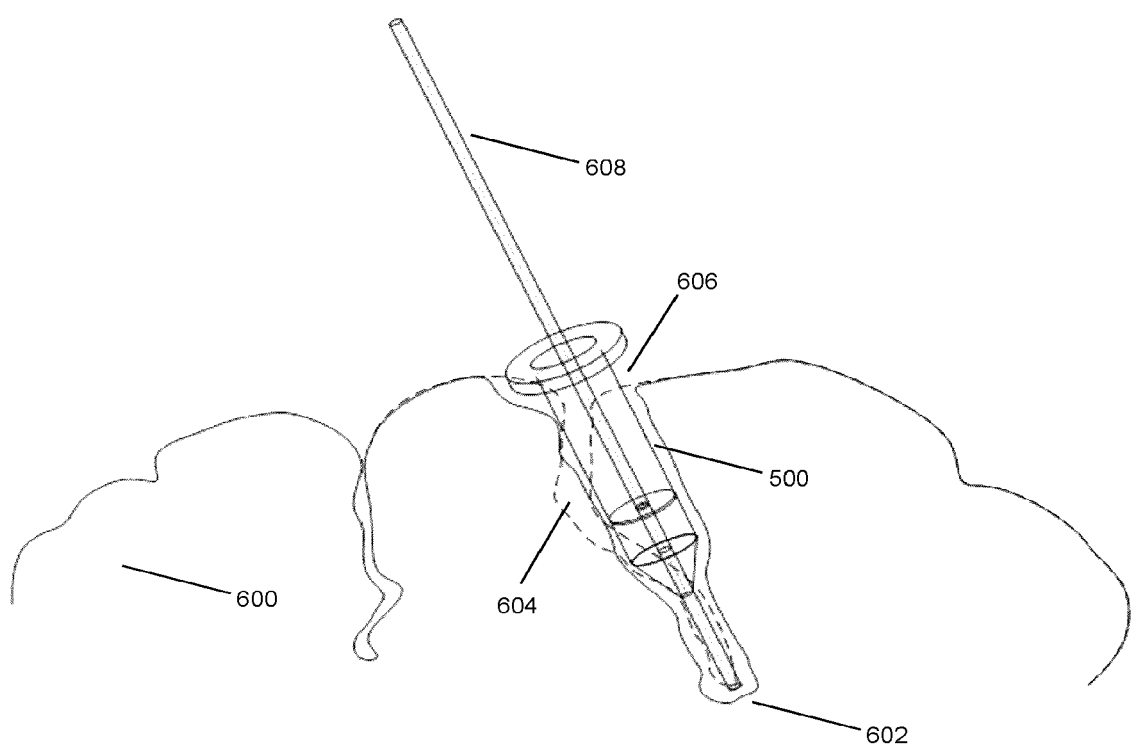
FIG. 6B illustrates the insertion of an access port and probe down a sulci path.

FIG. 6B illustrates the insertion of an access port and probe down a sulci path. In FIG. 6B, access port 500 is positioned to navigate a human brain 600. Positioned within access port 500 is medical instrument or probe 608. Probe 208 may be a resection tool, an image sensor and/or other types of sensing tools that can take measurements in different imaging modalities (e.g., ultrasound, Raman, OCT, PSOCT).

Probe 608 enters the brain 600 at sulci entry opening 606 and would like to navigate to targeted internal tissue 602. Ideally, probe 608 should follow sulci path 604, however, due to the linear nature of probe 606, a linear path (straight) to targeted internal tissue 602 is typically mapped out.

Figure 7:
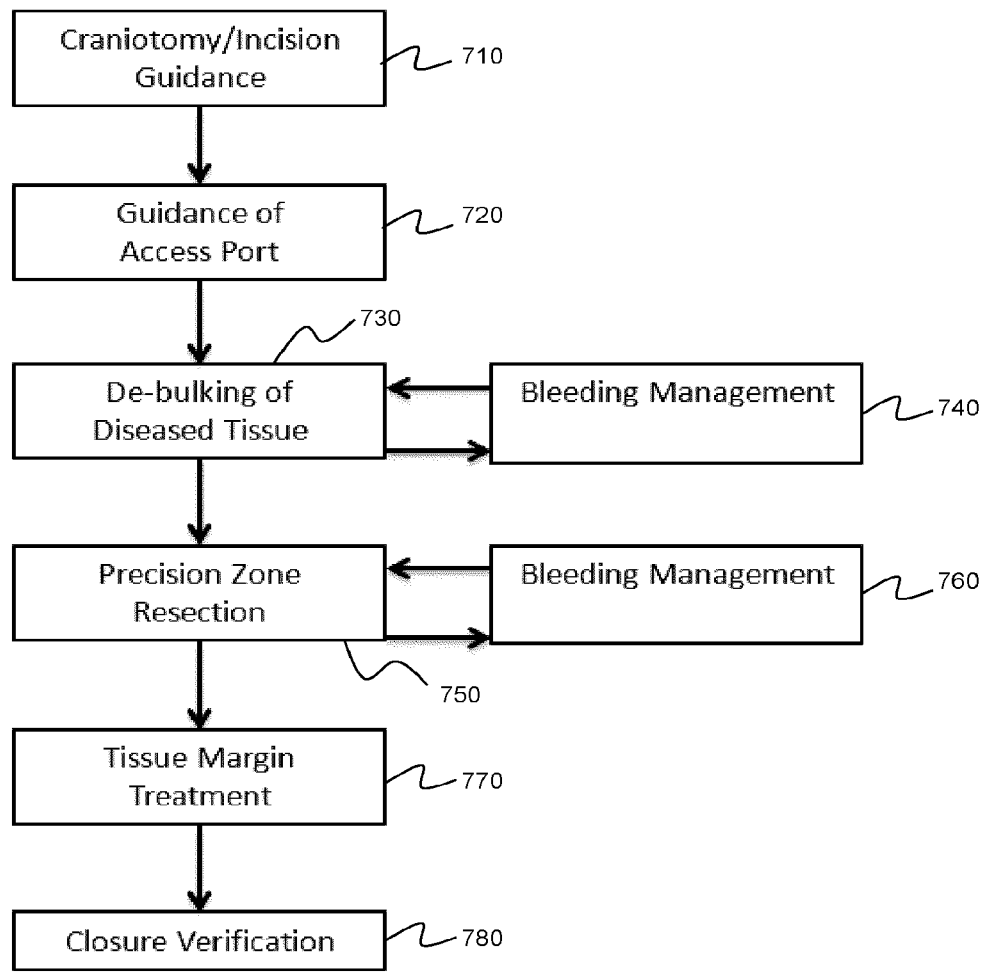
FIG. 7 illustrates the different steps of an example port based surgical procedure.

FIG. 7 illustrates the different steps of a port based surgical procedure. The first phase in the port based procedure is the incision of the scalp and craniotomy (step 710). During this stage (step 710), a bone flap is temporarily removed from the scalp to access the brain.

Once the incision and craniotomy (step 710) is completed the surgery enters the next phase "Guidance of Access Port" (step 720). During this phase the port is inserted into the brain until it reaches the desire target (usually tumor) depth.

The next simultaneous phases involves "De-bulking of Diseased Tissue" (step 730) and "Bleeding Management" (740). In the "De-bulking" phase (step 730), gross resection of unhealthy brain tissue is conducted using a suitable resection tool. In addition to the resection of the tissue (step 730), the surgeon also needs to managing any bleeding (step 740) that may occur within the surgical area of interest. During surgery a common occurrence is the rupturing of a blood vessel. If such a situation occurs, heavy bleeding precedes it, which can be problematic for viewing the surgical area of interest and closing the wound accordingly.

After the bulk resection phase (step 730), the surgical procedure enters the next two simultaneous phases of "Precision Zone Resection" or "fine-resection" (step 750) and further "Bleeding Management" (step 760). In this phase the surgeon removes the tumor from the fringes of healthy tissue, by differentitiating between the healthy and unhealthy tissue. During the fine-resection phase (step 750), medical instruments such as a Raman probe or PSOCT may be used to acquire spectra and utilize them to differntiate more effectively between healthy and unhealthy brain tissue at the boundary of a tumor. Further, other medical tools can be used to cauterize a blood vessel or other bodily tissue to effectively close the wound during the "Bleeding Management" phases (step 740 and 760).

The next phase of surgery involves "Tissue Margin Treatment" (step 770) where therapeutic agents may be administered at the surgical site to treat any remaining unhealthy tissue in the area and assure an optimal recovery of the patient.

The final step is "Closure Verification" (step 780) which involves the removal of the access port and closure of the wound. Further, any additional application of materials to assist in healing the surgical area may be applied (i.e., bandages, sutures, gauzes, healing creams, etc).

Figure 8A:
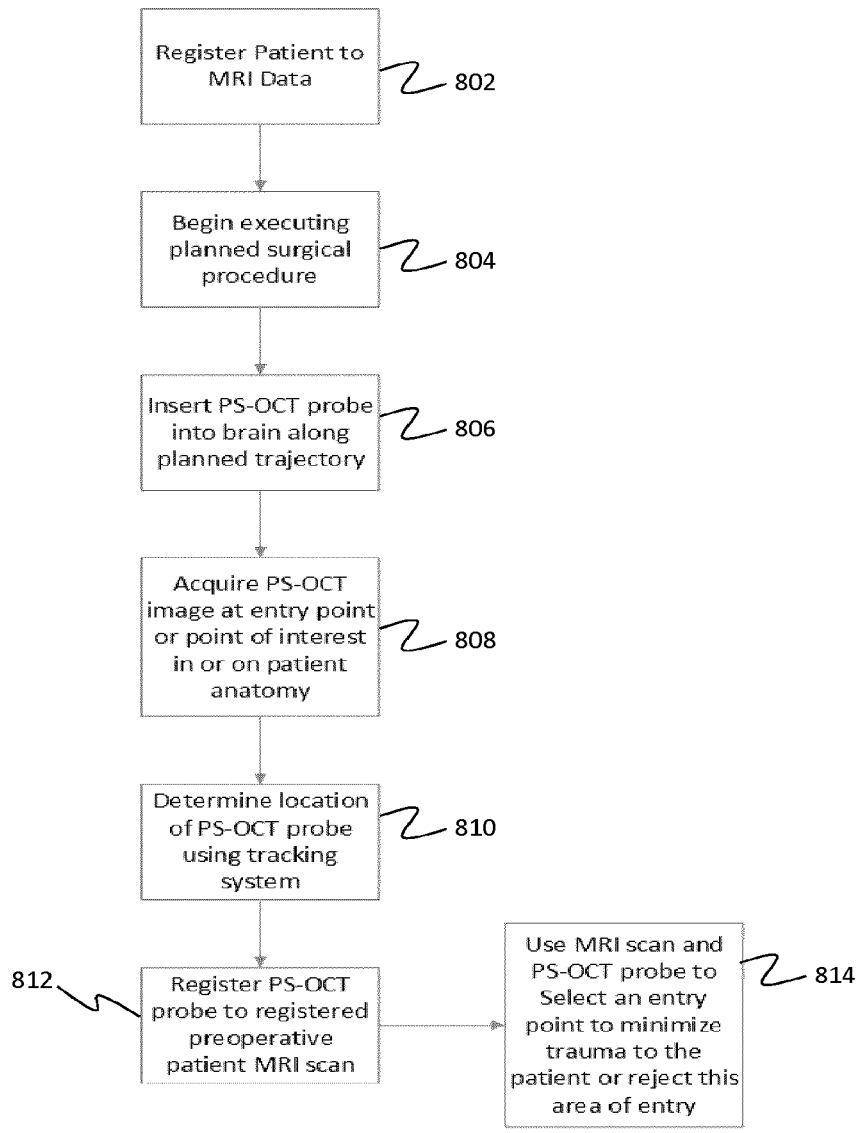
FIG. 8A illustrates an example process to acquire polarization-sensitive optical coherence tomorgraphy (PS-OCT) image.
Figure 8B:
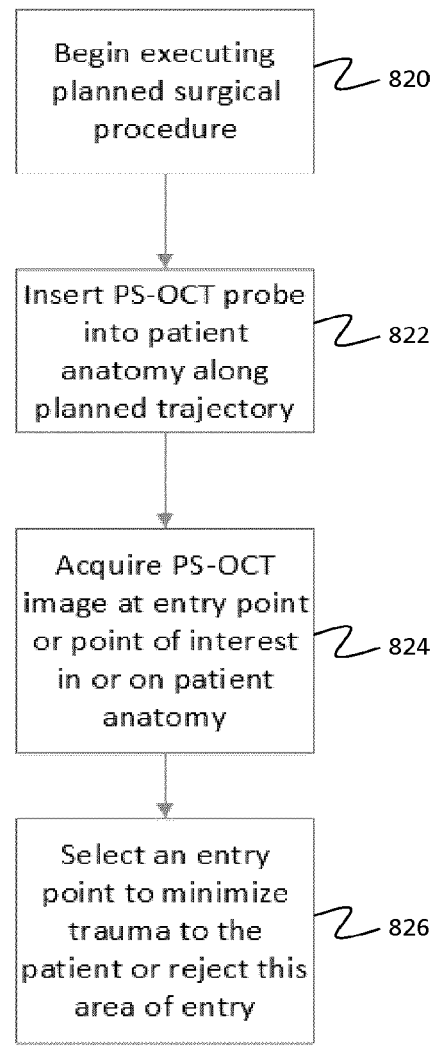
FIG. 8B illustrates an example general process for PS-OCT image acquisition.
Figure 8C:
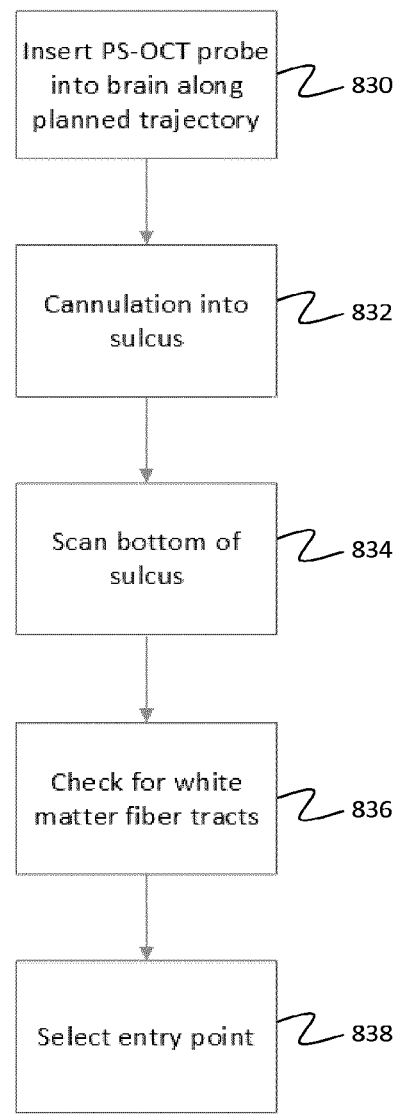
FIG. 8C illustrates an alternate example process for PS-OCT image acquisition.

FIGS. 8A-8C are example flow charts that illustrate process flow for acquiring PS-OCT images. FIG. 8A illustrates a process for acquiring an image. The process in FIG. 8A assumes that a neurosurgical plan is selected and has been created. The process begins at step 802 by spatially registering the patient to their pre-operative data (i.e., MRI or CT data) in image space, using for example a touch point or surface trace registration methodology as is commonly performed in concordance with the use of surgical navigation systems for image guided surgical procedures. Next, the execution of the planned surgical procedure is initiated in step 804. A PS-OCT probe is selected and inserted into the brain along the planned trajectory in step 806. A PS-OCT image is then acquired at the entry point or region of interest or on patient anatomy in step 808. The navigation system then determines the location of the PS-OCT probe using the navigation system's tracking cameras, at step 810.

The PS-OCT probe is then registered to the preoperative images/patient MRI scan in step 812. The pre-operative images are registered using the tracking feature of the navigation system in order to determine the location for initial registration. Finally, the intraoperatively acquired PS-OCT image is then combined (e.g. compared or fused) with the pre-operative MRI scan to select an entry point for the surgical procedure (target selection) in step 814. The combination of the pre-operative data and the intraoperative PS-OCT image target selection would minimize trauma to the patient. Further, this combined data can be used by the user (e.g. practitioner) to reject this area of entry of the data highlights risk.

FIG. 8B illustrates a general process for PS-OCT image acquisition. A surgical plan is also assumed to be created or selected. In step 820, a planned surgical procedure is initiated. The PS-OCT probe is then inserted into the brain along the planned trajectory in step 822. A PS-OCT image is acquired at the entry point or at the region of interest or on the patient anatomy at step 824. Finally, an entry point is selected at step 826, where the entry point is selected to reduce or minimize trauma to the subject. The area of entry shall may be rejected if risk is determined.

FIG. 8C illustrates an alternate process for PS-OCT image acquisition for access port based procedures. Minimally invasive brain surgery using access ports is a recently conceived method of performing surgery on brain tumors previously considered inoperable. To address intracranial surgical concerns, specific products such as the NICO Brain-Path™ port have been developed for port-based surgery. In FIG. 8C, a surgical plan is also assumed to be created or selected. Step 830 involves executing a planned surgical procedure. The PS-OCT probe is then inserted into the brain along the planned trajectory in step 832. Thereafter, the cannulation process is initiated in step 832. Cannulation involves inserting a port into the brain, typically along a sulci path, along a trajectory plan. Cannulation is an iterative process that involves repeating the steps of aligning the port on engagement and setting the planned trajectory and then cannulating to the target depth until the complete trajectory plan is executed. Once the port is aligned with the first path trajectory segment the surgeon begins the cannulation procedure and moves the port introducer along the first segment while the system and method assists the surgeon in remaining consistently coaxial with the path segment and displays to the surgeon the distance of the introducer along the first segment until the end of the segment is reached. The surgeon then changes direction to follow the second trajectory segment. The process is repeated until the target location is reached.

Step 836 involves scanning the bottom of the sulcus and acquiring a PS-OCT image. In step 836, the image is processed to identify the presence of fiber tracts as described in further detail above. Finally, a desirable insertion point is selected based on the image in step 838.

As described above, various embodiments of the present disclosure may be employed for the detection of a wide variety of anisotropic structures, and the systems and methods described herein may be adapted for a wide variety of applications. Some non-limiting example applications include: brain surgery, including port-based brain surgery, deep brain simulation delivery, endo-nasal surgery, surgical resection (general resection to show areas where the white matter is sparse), and radiation therapy delivery (e.g. high-localized dose delivery); cardiac surgery, such as pacemaker placement and AF ablations; head and neck surgery, such as tumor resection; spine surgery, such as tumor resection, pain management and nerve damage; and prostate resection (systems and methods disclosed herein may be adapted to help remove the tumor from around the nerves).

In a deep brain simulation procedure, the placement of the electrode leads in the brain are critical for high quality regulation of brain activities. Deep brain stimulation (DBS) is a surgical procedure to implant a pacemaker-like device that sends electrical signals to brain areas that are thought to be partially responsible for body movement. Electrodes are placed deep in the brain and are connected to a stimulator device. Similar to a heart pacemaker, a neuro-stimulator uses electric pulses to help regulate brain activity. In deep brain stimulation, electrodes are placed in a specific area of the brain (usually the subthalamic nucleus (STN)) depending on the symptoms being treated. Right above and below the subthalmic nucleus, a layer of white matter tracts is present as part of the internal capsule of the brain. Through using a navigation system, the placement of the electrode can be close to the subthalamic nucleus but precise targeting and hitting of the subthalamic nucleus is never certain due to its small size (~few millimeters in length and width). Real time intraoperative imaging is also not possible due to the small incision into the brain to avoid brain damage. Listening to the electrical signal from the electrode through neuron firing is the only presently employed way to identify and confirm the placement of the electrode. However, this requires highly trained personelle. Moreover, no direction is suggested from the devices for repositioning the electrode when it is not placed in or near the subthalamic nucleus.

Consequently the use of OCT probe described herein may help optimize positioning of the electrode. This may be accomplished as follows. First the OCT probe is place near the subthalamic nucleus through the tracked cannula used in electrode placement. The cannula usually directs the lead, and the probe in this case, to about 10 to 25 mm away from the subthalamic nucleus. From there on, the OCT probe will image and proceed forward till it images white matter tracts.

The PSOCT image acquisition in this case may allow non-traumatic visualization of the white matter tracts within the vicinity of the STN, allowing in some cases a confirmation of a placement of the probe in the optimally achievable position. This may be achieved once the probe images the white matter tracts by proceeding slightly forward until it sees grey matter and then white matter again to confirm the location of the subthalamic nucleus. The steps described here are specifically for placement of an electrode in the STN wherein the direction of approach passes through white matter than STN and again through white matter as is the anatomy during commonly performed procedures. It should be noted that placement of any DBS electrode through any applicable anatomy having white matter landmarks is also contemplated by the system described herein and the example provided should not be taken to limit the scope of the application of the system as described. After the location is identified, the probe can then be replaced with an electrode lead to further confirm the location through listening to the electrical signal from electron firing in the vicinity of the STN. Once it is confirmed, the simulation process can proceed.

EXAMPLES

Figure 9A:
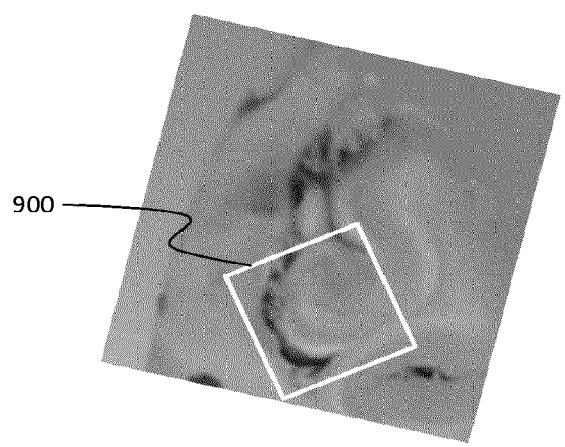
FIG. 9A is an image of a tissue sample.

FIG. 9A depicts a tissue sample (a slice of human brain) with a square 900 indicating the area where images 905, 910, 915, and 920 were taken.

Figure 9B:
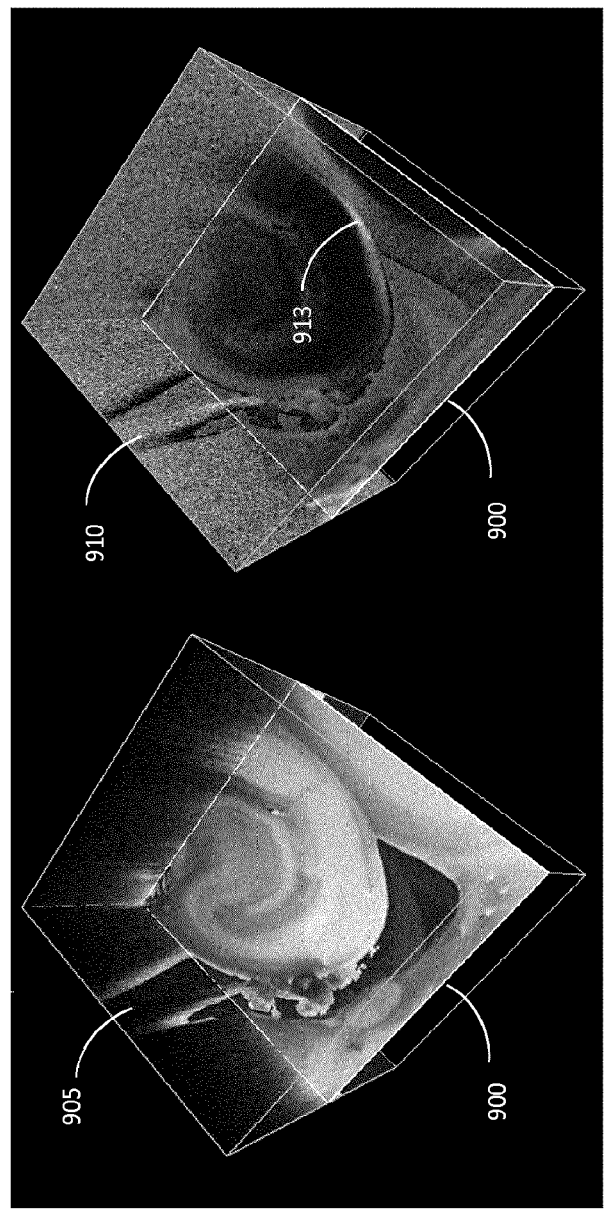
FIG. 9B illustrates example OCT images of the tissue region shown in FIG. 9A.
Figure 9C:
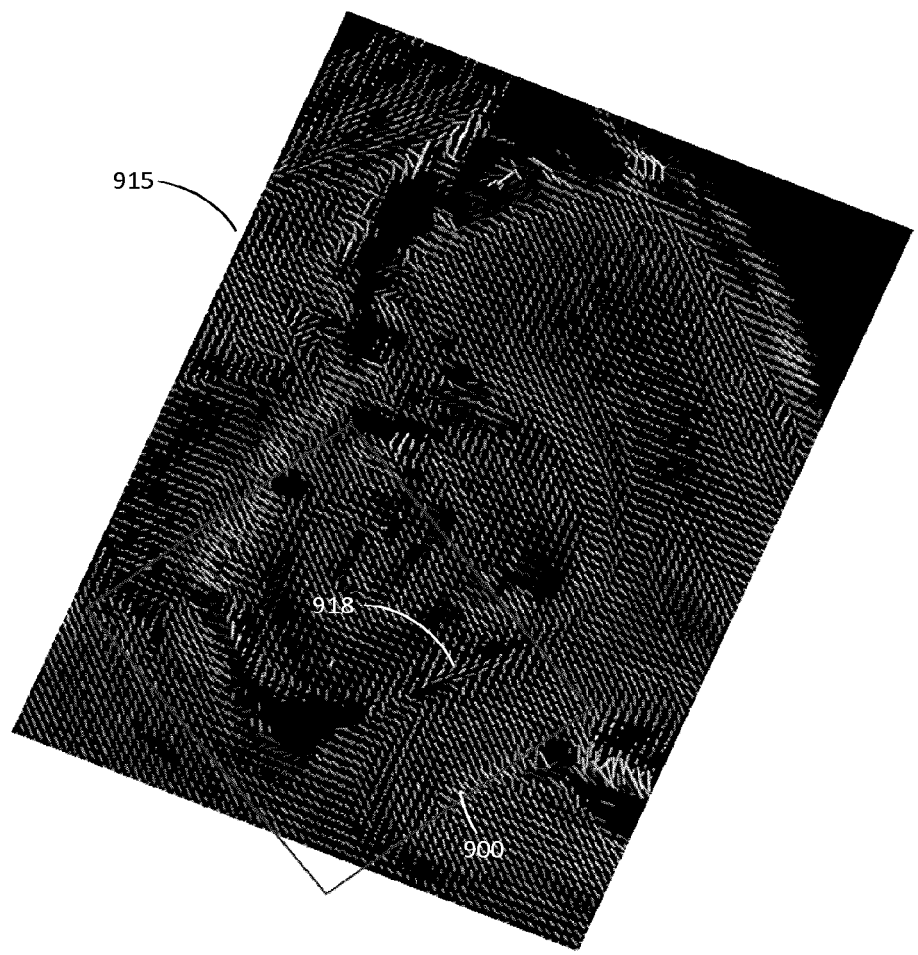
FIG. 9C illustrates example MRI images of the tissue region shown in FIG. 9A.
Figure 9D:
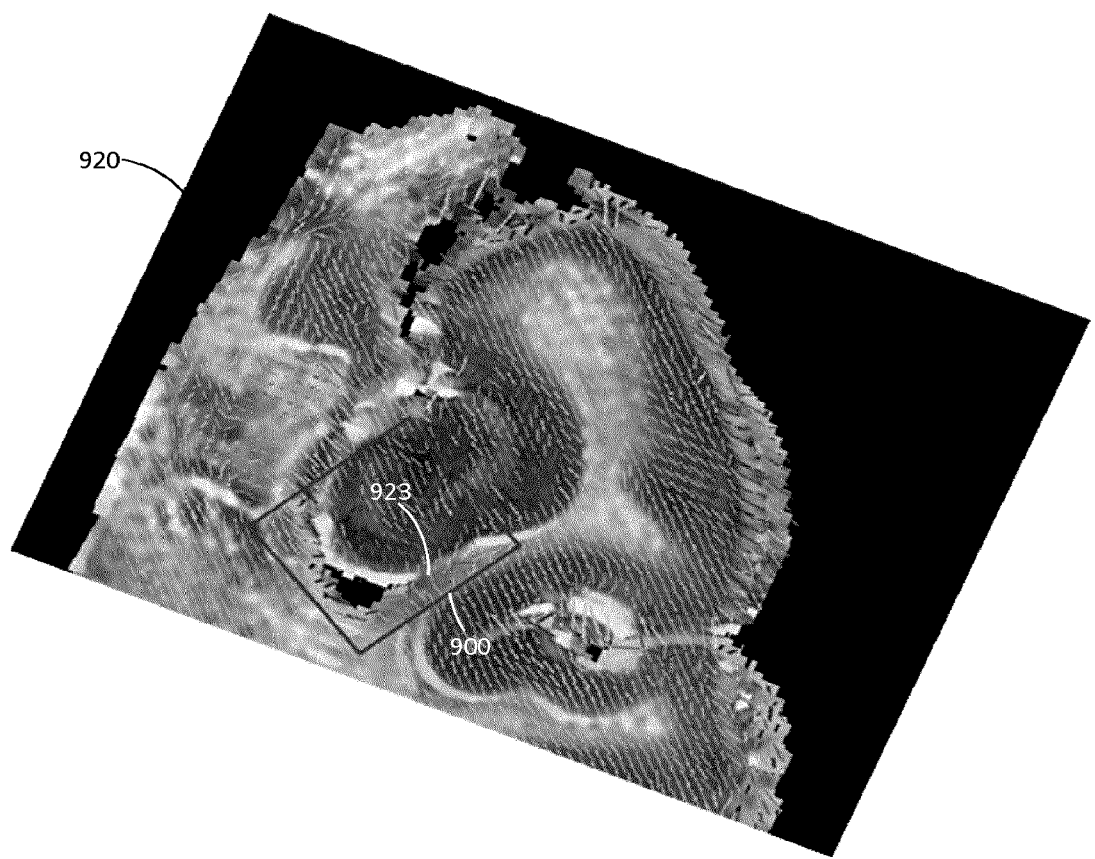
FIG. 9D illustrates example OCT images of the tissue region shown in FIG. 9A.

FIG. 9B illustrates sample OCT images created from the tissue sample shown in FIG. 9A. The top left image 905 of FIG. 9B, shows a conventional reflectivity OCT image with contrast based on intensity data of the area 900 of the tissue sample. The right image 910 illustrates a PS-OCT image with contrast based on retardance data. Where retardance measures the degree of organization of the sample. In this case, the brightness in the image shows the strength of organization which is substantially proportional to the magnitude of the tensors shown in the MRI tensor image 915 in FIG. 9C. The overlaid vectors on the retardance image 920 depicted in FIG. 9D shows the spatially averaged orientation encoded map from OCT acquisition. The vectors in this image 920 show the direction of the white matter tracts on the x-y plane similar to the projected diffusion tensor imaging (DTI) image 915 shown on the same sample. The combined tensor with voxel magnitude values are similar to the combined retardation and direction values from the orientation data providing a similar tractography metric as DTI images. For example, in one particular spot, the vectors 918 in the MRI tensor image 915 shows that fiber tracts are on the imaging plane with a strong degree of directionality. This is reflected in the retardation image 910 as can be seen in the bright spot 913, and also in the overlaid retardance image 920 in the area 923.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

What is therefore claimed is:

1. A method of identifying a suitable surgical location for proceeding with a surgical procedure based on local polarization-sensitive optical coherence tomography imaging, the method comprising:

obtaining one or more polarization-sensitive optical coherence tomography images of a tissue region;

processing the one or more polarization-sensitive optical coherence tomography images to generate local volumetric image data, the local volumetric image data providing a spatial map of anisotropic structure within the tissue region;

processing the local volumetric image data to determine one or more suitable surgical locations for avoiding or reducing damage to local anisotropic tissue structure identified within the tissue region when proceeding with the surgical procedure; and generating a composite image based on the local volumetric image data and the pre-operative volumetric image data which may then be presenting the composite image on a display device;

identifying at least one suitable surgical location on the display device;

wherein the at least one surgical location is identified on a displayed image that is generated based on the pre-operative image data;

wherein the pre-operative image data is provided in a patient reference frame, and wherein the one or more polarization-sensitive optical coherence tomography images are obtained with a spatially tracked polarization-sensitive optical coherence tomography probe, and wherein a tracked position and orientation of the spatially tracked polarization-sensitive optical coherence tomography probe may be tracked relative to a global reference frame that can be referenced to a patient reference frame allowing the tissue region to be located within the patient reference frame to transform the local volumetric image data into the patient reference frame;

wherein the tissue is brain tissue, wherein the local anisotropic tissue structure are fiber tracts, and wherein the displayed image includes pre-operative tractography information of the fiber tracts.

2. The method according to claim 1 wherein the tractography information is generated based on the pre-operative image data and the local volumetric image data.

3. The method according to claim 1 wherein the tissue is brain tissue and wherein the local anisotropic tissue structure comprises fiber tracts.

4. The method according to claim 1 wherein the local anisotropic tissue structure comprises at least one anisotropic tissue structure selected from the group consisting of nerve tissue structure, spinal tissue structure, muscle tissue structure, tendon tissue structure, and ligament tissue structure.

5. The method according to claim 1 wherein the tissue region is exposed by a surgical access port.

6. The method according to claim 1 wherein the tissue region comprises a tissue volume residing below an exposed tissue surface.

7. The method according to claim 6 wherein the tissue region further comprises the exposed tissue surface.

* * * * *